(12) United States Patent
Oshiro et al.

(10) Patent No.: US 11,945,932 B2
(45) Date of Patent: Apr. 2, 2024

(54) PLASTICIZER FOR HALOGEN RESINS

(71) Applicant: KAO CORPORATION, Tokyo (JP)

(72) Inventors: Kojun Oshiro, Wakayama (JP);
Munehisa Okutsu, Takaishi (JP)

(73) Assignee: KAO CORPORATION, Tokyo (JP)

( * ) Notice: Subject to any disclaimer, the term of this patent is extended or adjusted under 35 U.S.C. 154(b) by 758 days.

(21) Appl. No.: 16/978,534

(22) PCT Filed: Feb. 13, 2019

(86) PCT No.: PCT/JP2019/004963
§ 371 (c)(1),
(2) Date: Sep. 4, 2020

(87) PCT Pub. No.: WO2019/171890
PCT Pub. Date: Sep. 12, 2019

(65) Prior Publication Data
US 2021/0017357 A1 Jan. 21, 2021

(30) Foreign Application Priority Data
Mar. 8, 2018 (JP) .................. 2018-042114

(51) Int. Cl.
| | | |
|---|---|---|
| C08K 5/12 | (2006.01) | |
| C08K 5/00 | (2006.01) | |
| C08L 11/00 | (2006.01) | |
| C08L 27/06 | (2006.01) | |
| C08L 27/08 | (2006.01) | |

(52) U.S. Cl.
CPC ............ C08K 5/12 (2013.01); C08K 5/0016 (2013.01); C08L 11/00 (2013.01); C08L 27/06 (2013.01); C08L 27/08 (2013.01); C08L 2201/08 (2013.01); C08L 2203/202 (2013.01)

(58) Field of Classification Search
CPC .. C08K 5/12; C08K 5/0016; C08K 2201/014; C08L 11/00; C08L 27/06; C08L 27/08; C08L 2201/08; C08L 2203/202
See application file for complete search history.

(56) References Cited

U.S. PATENT DOCUMENTS

| | | | |
|---|---|---|---|
| 3,094,503 A | 6/1963 | Jacocks et al. | |
| 5,268,514 A * | 12/1993 | Bahrmann | C07C 45/50 568/840 |
| 5,516,948 A | 5/1996 | Bahrmann et al. | |
| 6,482,972 B1 * | 11/2002 | Bahrmann | C07C 45/74 560/76 |
| 7,300,966 B2 * | 11/2007 | Breitscheidel | C07C 29/141 560/76 |
| 8,907,217 B2 | 12/2014 | Abu-Ali et al. | |
| 2014/0336319 A1 | 11/2014 | Kim et al. | |
| 2016/0272780 A1 | 9/2016 | Kim et al. | |
| 2017/0349727 A1 | 12/2017 | Oshiro et al. | |

FOREIGN PATENT DOCUMENTS

| | | | |
|---|---|---|---|
| CN | 85101806 A | 1/1987 | |
| CN | 105860328 A | 8/2016 | |
| IN | 201717020133 | 8/2017 | |
| JP | 1-104265 A | 4/1989 | |
| JP | 2-152455 A | 6/1990 | |
| JP | 2-209838 A | 8/1990 | |
| JP | 5-194761 A | 8/1993 | |
| JP | 6-166644 A | 6/1994 | |
| JP | 7-39361 B2 | 5/1995 | |
| JP | 7-173356 A | 7/1995 | |
| JP | 7-304918 A | 11/1995 | |
| JP | 8-3401 A | 1/1996 | |
| JP | 2001-2829 A | 1/2001 | |
| JP | 3139141 B2 | 2/2001 | |
| JP | 3832143 B2 * | 10/2006 | ............... C08K 5/05 |
| JP | 2015-520185 A | 7/2015 | |
| JP | 2016-188299 A | 11/2016 | |
| JP | 2017-509592 A | 4/2017 | |
| WO | WO2016/098496 A1 | 6/2016 | |

OTHER PUBLICATIONS

Machine translation JP 2001002829 A to Takeuchi et al., published Jan. 9, 2001 (Year: 2001).*
Machine translation JP 3832143 B2 to Asai et al., published Oct. 11, 2006 (Year: 2006).*

(Continued)

*Primary Examiner* — Jane L Stanley
(74) *Attorney, Agent, or Firm* — Birch, Stewart, Kolasch & Birch, LLP

(57) ABSTRACT

The present invention relates to [1] a plasticizer for a halogen-based resin containing a mixture of didecyl phthalates each containing a linear or branched $C_{10}$ alkyl group, in which a content of di-n-decyl phthalate in the mixture is not less than 48 mol % and not more than 70 mol %; [2] a plasticizer composition for a halogen-based resin containing the aforementioned plasticizer; and [3] a halogen-based resin composition containing a halogen-based resin and the aforementioned plasticizer. The plasticizer of the present invention has an excellent plasticizing effect on a halogen-based resin and at the same time, can exhibit excellent effects of improving all of productivity, processability, kneading properties and heat resistance without deterioration in the respective properties.

15 Claims, No Drawings

(56) References Cited

OTHER PUBLICATIONS

International Search Report, issued in PCT/JP2019/004963, PCT/ISA/210, dated Apr. 16, 2019.
Extended European Search Report for European Application No. 19764001.4, dated Oct. 20, 2021.
Chen et al., "Study on the Synthesis of DIDP with Solid Acid as Catalyst," Acta Scientiarum Naturalium Universitatis Nankaiensis, vol. 42, No. 3, Jun. 2009, 5 pages total, with an English abstract.
Beom-Seok, et al., "Evaluation of the Carcinogenicity of Diisodecyl Phthalate (DIDP), a Plasticizer, in Rats," Toxicologic Pathology, vol. 36, No. 1, 2008, pp. 149-150, 28 pages total.

* cited by examiner

PLASTICIZER FOR HALOGEN RESINS

FIELD OF THE INVENTION

The present invention relates to a plasticizer for a halogen-based resin which contains didecyl phthalates, a plasticizer composition for a halogen-based resin which contains the plasticizer, and a halogen-based resin composition.

BACKGROUND OF THE INVENTION

A halogen-based resin such as polyvinyl chloride (PVC), etc., is an important resin used as a general-purpose polymer in various application fields. For example, the halogen-based resin is used in the form of hard PVC, soft PVC, etc., in the application fields such as pipes, building materials, packaging materials, agricultural materials, sheathing materials for electric cables, interior materials, wall paper materials, etc. For the purposes of mainly improving processability of the halogen-based resin and imparting good flexibility to a final product obtained from the halogen-based resin, a plasticizer is added to the halogen-based resin.

As the plasticizer, phthalate-based plasticizers (such as dioctyl phthalate (DOP), diisononyl phthalate (DINP) and the like) have been generally used conventionally. However, these phthalate-based plasticizers tend to have a risk of causing toxicity to environments. For this reason, in recent years, it has been required that the phthalate-based plasticizers are replaced with the other plasticizers that are capable of maintaining a good performance similar to that of the phthalate-based plasticizers.

As the non-phthalate-based plasticizers, there are known acetyl tributyl citrate (ATBC), di 2-ethylhexyl adipate (DOA), tri 2-ethylhexyl trimellitate (TOTM), etc. However, these non-phthalate-based plasticizers are deteriorated in their performance as compared to the phthalate-based plasticizers. For example, ATBC is deteriorated in heat resistance, DOA is deteriorated in compatibility with the vinyl chloride-based resin, and TOTM is deteriorated in plasticization efficiency.

JP 2-209838A (Patent Literature 1) discloses a plasticizer that is produced by subjecting a $C_{10}$ alcohol mixture containing 2-propyl heptanol as a main component and a carboxylic acid to esterification reaction.

JP 5-194761A (Patent Literature 2) discloses a vinyl chloride resin film that contains a plasticizer constituted of a phthalic acid diester of a mixed decyl alcohol containing not less than 89% by weight of 2-propyl heptanol and not more than 10% by weight of 4-methyl-2-propyl hexanol, and a vinyl chloride resin.

JP 2001-2829A (Patent Literature 3) discloses a phthalic acid diester plasticizer composition that is obtained by reacting a $C_{10}$ aliphatic alcohol composition in which a weighted mean value of sums of chemical bond numbers of respective aliphatic alcohols therein lies within a specific range, with phthalic acid or phthalic anhydride, and a vinyl chloride-based resin composition.

SUMMARY OF THE INVENTION

The present invention relates to a plasticizer for a halogen-based resin which contains a mixture of didecyl phthalates each containing a linear or branched $C_{10}$ alkyl group, in which a content of di-n-decyl phthalate in the mixture is not less than 48 mol % and not more than 70 mol %.

DETAILED DESCRIPTION OF THE INVENTION

The plasticizers described in the aforementioned Patent Literatures 1 to 3 have poor compatibility with a halogen-based resin, and also have failed to exhibit satisfactory plasticization efficiency. Thus, these plasticizers have such a problem that if it is intended to allow the plasticizers to exhibit excellent plasticization effect at a level identical to or higher than that of the phthalate-based plasticizers, the resulting resin compositions tend to suffer from deterioration in their properties such as processability, kneading properties, heat resistance, etc.

The present invention relates to a plasticizer for a halogen-based resin which has an excellent plasticization effect on the halogen-based resin and at the same time, can exhibit excellent effects of improving all of productivity, processability, kneading properties and heat resistance of the resulting resin composition without deterioration in the respective properties, and a halogen-based resin composition containing the plasticizer.

The present inventors have found that the plasticizer for a halogen-based resin having a di-n-decyl phthalate content that lies within a specific range is capable of solving the aforementioned conventional problems.

That is, the present invention relates to the following aspects [1] to [3].

- [1] A plasticizer for a halogen-based resin containing a mixture of didecyl phthalates each containing a linear or branched $C_{10}$ alkyl group, in which a content of di-n-decyl phthalate in the mixture is not less than 48 mol % and not more than 70 mol %.
- [2] A plasticizer composition for a halogen-based resin containing the plasticizer according to the above aspect [1].
- [3] A halogen-based resin composition containing a halogen-based resin, and the plasticizer according to the above aspect [1] or the plasticizer composition according to the above aspect [2].

In accordance with the present invention, it is possible to provide a plasticizer for a halogen-based resin which has an excellent plasticizing effect on the halogen-based resin and at the same time, can exhibit excellent effects of improving all of productivity, processability, kneading properties and heat resistance of the resulting resin composition without deterioration in the respective properties, and a halogen-based resin composition containing the plasticizer.

[Plasticizer for Halogen-Based Resin]

The plasticizer for a halogen-based resin according to the present invention (hereinafter also referred to merely as a "plasticizer") is characterized by containing a mixture of didecyl phthalates each containing a linear or branched $C_{10}$ alkyl group, in which a content of di-n-decyl phthalate in the mixture is not less than 48 mol % and not more than 70 mol %.

The plasticizer of the present invention has an excellent plasticization effect on a halogen-based resin and at the same time, can exhibit excellent effects of improving all of productivity, processability, kneading properties and heat resistance of the resulting resin composition without deterioration in the respective properties. The reason why the aforementioned excellent effects can be attained by the present invention is considered as follow though it is not necessarily clearly determined yet.

That is, the specific mixture of didecyl phthalates as the plasticizer of the present invention contains functional groups at ortho positions of the benzene ring which are each a $C_{10}$ alkyl group. For this reason, the plasticizer can be improved in compatibility with the halogen-based resin and therefore can be dispersed in the halogen-based resin in a well-balanced manner to thereby exhibit a good plasticization effect on the halogen-based resin. Moreover, it is considered that since a specific ratio of the functional groups has a linear alkyl structure, it is possible to widen a distance between polymer chains in the halogen-based resin, so that the plasticization effect of the plasticizer on the halogen-based resin can be enhanced.

If the di-n-decyl phthalate only is used as the plasticizer, coagulation between molecules of the plasticizer tends to proceed, so that the plasticizer tends to suffer from unevenness of distribution in the halogen-based resin even when being kneaded together therewith. However, it is considered that since a specific amount of the bulky didecyl phthalate having a branched structure is contained in the plasticizer, the resulting plasticizer can be dispersed in the halogen-based resin with low energy without coagulation thereof and therefore can exhibit its inherent plasticization effect, so that the resulting resin composition can be improved in productivity, processability and kneading properties.

Furthermore, it is considered that since the di-n-decyl phthalate has low volatility, the resulting resin composition can be improved in heat resistance.

<Mixture of Didecyl Phthalates>

The mixture of didecyl phthalates according to the present invention is in the form of a mixture of didecyl phthalates each containing a linear or branched $C_{10}$ alkyl group, which are each represented by the following general formula (1).

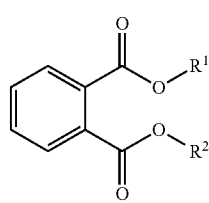

(1)

In the formula (1), $R^1$ and $R^2$ are each independently a linear or branched $C_{10}$ alkyl group from the viewpoint of improving all of plasticizability, productivity, processability, kneading properties and heat resistance of the resulting halogen-based resin composition.

The mixture of didecyl phthalates that are each represented by the general formula (1) is in the form of a mixture containing the following compounds (i) to (iii).

(i) Di-n-decyl phthalate represented by the following formula (2) in which the substituent groups $R^1$ and $R^2$ of the formula (1) corresponding to the didecyl group both are an n-decyl group.

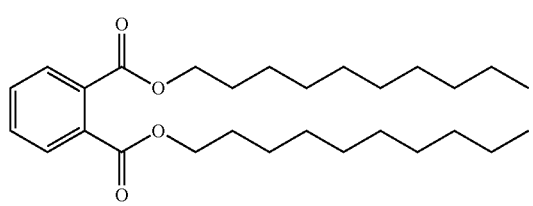

(2)

(ii) Compound of the formula (1) in which one of the substituent groups $R^1$ and $R^2$ is an n-decyl group, and the other thereof is a branched decyl group.

(iii) Compound of the formula (1) in which both of the substituent groups $R^1$ and $R^2$ are branched decyl groups.

(Production of Mixture of Didecyl Phthalates)

The mixture of didecyl phthalates is produced in the form of an intermolecular condensation reaction product by subjecting a phthalic acid raw material and an alcohol raw material to esterification reaction.

The esterification reaction as described herein includes a direct esterification reaction between the phthalic acid raw material and the alcohol raw material, an ester exchange reaction between a phthalic acid ester and an alcohol, and the like.

Among the aforementioned esterification reactions, the direct esterification reaction between the phthalic acid raw material and the alcohol raw material is preferred from the viewpoint of improving the reactivity and productivity.

(Phthalic Acid Raw Material)

Examples of the phthalic acid raw material include phthalic acid, phthalic anhydride, phthalic acid esters such as dimethyl phthalate, and the like. Among these phthalic acid raw materials, from the viewpoint of improving the availability and productivity, preferred is at least one compound selected from the group consisting of phthalic acid and phthalic anhydride, and more preferred is phthalic anhydride.

(Alcohol Raw Material)

Examples of the alcohol raw material include n-decanol (linear alcohol), a branched alcohol, and a mixture of these alcohols. As the alcohol raw material, any suitable alcohol may be used as long as it is in the form of an alcohol containing a $C_{10}$ alkyl group.

As the n-decanol, there may be used any of a synthesized alcohol that is produced from an olefin, etc., as a raw material by a synthesis method such as an oxo method, and a vegetable-derived alcohol obtained by subjecting fats and oils such as coconut oil, etc., to hydrolysis.

Examples of the branched alcohol include at least one alcohol selected from the group consisting of isodecanol (8-methyl-1-nonanol); secondary decanols such as 2-decanol, 3-decanol, 4-decanol and 5-decanol; and 2-propyl-1-heptanol, 4-methyl-2-propyl-1-hexanol, etc.

Examples of commercially available products of the n-decanol include "KALKOL 1098" (tradename) available from Kao Corporation, and the like. Examples of commercially available products of the branched alcohol include "ISODECANOL" (tradename; mixture of isomers of decanol) available from KH NeoChem Co., Ltd., "2-PROPYL HEPTANOL" (tradename; mixture of 2-propyl heptanol and 4-methyl-2-propyl hexanol (molar ratio=95:5)) available from BASF, and the like.

(Method for Production of Plasticizer)

As the method for producing the plasticizer of the present invention, there may be mentioned, for example, the following methods (i) and (ii).

(i) Method of producing the plasticizer by using a mixed decanol as a raw material in which a content of n-decanol in the alcohol raw material is preciously controlled such that a content of di-n-decyl phthalate in the plasticizer is not less than 48 mol % and not more than 70 mol % after producing the plasticizer.

(ii) Method of producing the plasticizer by adding and mixing di-n-decyl phthalate such that a content of the di-n-decyl phthalate in the plasticizer is adjusted to a predetermined value.

The content of the di-n-decyl phthalate in the mixture of didecyl phthalates is not less than 48 mol % and not more than 70 mol %, preferably not less than 50 mol % and more preferably not less than 52 mol % from the viewpoint of improving processability, kneading properties and heat resistance of the resulting halogen-based resin composition. The content of the di-n-decyl phthalate in the mixture of didecyl phthalates is also preferably not more than 65 mol % and more preferably not more than 60 mol % from the viewpoint of enhancing productivity of the halogen-based resin composition.

(Didecyl Phthalate(s) Other than Di-n-Decyl Phthalate)

The plasticizer of the present invention contains didecyl phthalate(s) other than the di-n-decyl phthalate. Such didecyl phthalates may include didecyl phthalates represented by the aforementioned general formula (1) in which $R^1$ and $R^2$ are identical to each other, and didecyl phthalates represented by the general formula (1) in which $R^1$ and $R^2$ are different from each other.

Examples of the didecyl phthalates represented by the general formula (1) in which $R^1$ and $R^2$ are identical to each other include di-1-methylnonyl phthalate, di-1-ethyloctyl phthalate, di-1-propylheptyl phthalate, di-1-butylhexyl phthalate, di-isodecyl phthalate, di-2-propylheptyl phthalate, di-4-methyl-2-propylhexyl phthalate, and the like.

Examples of the didecyl phthalates represented by the general formula (1) in which $R^1$ and $R^2$ are different from each other include n-decyl (1-methylnonyl) phthalate, n-decyl (1-ethyloctyl) phthalate, n-decyl (1-propylheptyl) phthalate, n-decyl (1-butylhexyl) phthalate, n-decyl (isodecyl) phthalate, n-decyl (2-propylheptyl) phthalate, n-decyl (4-methyl-2-propylhexyl) phthalate, isodecyl (2-propylheptyl) phthalate, isodecyl (4-methyl-2-propylhexyl) phthalate, and the like.

Among these didecyl phthalates, from the viewpoint of improving plasticizability, productivity, processability, kneading properties and heat resistance of the resulting halogen-based resin composition, it is preferred that the plasticizer contains at least one compound selected from the group consisting of di-2-propylheptyl phthalate and n-decyl (2-propylheptyl) phthalate.

(Esterification Reaction Conditions)

(Amounts of Raw Materials Charged)

The amount of the alcohol raw material charged at the time of initiation of the esterification reaction is preferably an excessive amount relative to a stoichiometric amount thereof. The stoichiometric amount of the alcohol raw material used in the esterification reaction means a theoretical ratio thereof capable of producing the phthalic acid raw material, and corresponds to a molar amount 2 times that of the phthalic acid raw material used.

That is, the amount of the alcohol raw material charged is preferably not less than 2.0 mol, more preferably not less than 2.1 mol, even more preferably not less than 2.2 mol and further even more preferably not less than 2.3 mol on the basis of 1 mol of the phthalic acid raw material from the viewpoint of promoting and completing the esterification reaction, and is also preferably not more than 10 mol, more preferably not more than 6 mol, even more preferably not more than 4 mol and further even more preferably not more than 3 mol on the basis of 1 mol of the phthalic acid raw material from the viewpoint of promoting the esterification reaction and removing an excessive amount of the alcohol remaining after completion of the esterification reaction.

It is preferred that the content of water in the alcohol raw material used is reduced as small as possible. If a large amount of water is contained in the alcohol raw material, there tends to occur such a risk that the water causes the below-mentioned toxicity to a catalyst, and therefore the catalyst used in the reaction suffers from deterioration in catalytic activity.

(Catalyst)

As the esterification catalyst used in the aforementioned esterification reaction, there may be used known esterification catalysts having good esterification capability. Of these esterification catalysts, preferred are organic metal catalysts.

Examples of the organic metal catalysts include at least one compound selected from the group consisting of organic tin compounds such as tin tetraethylate, butyl tin maleate, dimethyl tin oxide, monobutyl tin oxide, dibutyl tin oxide and dioctyl tin oxide; organic titanium compounds such as tetraisopropyl titanate; organic zinc compounds such as zinc acetate; and the like.

Of these organic metal catalysts, from the viewpoint of high reaction efficiency, etc., preferred are organic tin compounds, more preferred is at least one tin oxide compound selected from the group consisting of dimethyl tin oxide, monobutyl tin oxide, dibutyl tin oxide, dioctyl tin oxide, etc., even more preferred is at least one tin oxide compound selected from the group consisting of monobutyl tin oxide and dibutyl tin oxide, and further even more preferred is monobutyl tin oxide.

In addition, from the viewpoint of high productivity, preferred are the organic titanium compounds, and more preferred is at least one compound selected from the group consisting of tetraisopropyl titanate, tetra-n-butyl titanate and tetra-2-ethylhexyl titanate.

The amount of the catalyst used in the esterification reaction may vary depending upon the kind thereof, and is preferably not less than 0.01 part by mass, more preferably not less than 0.02 part by mass and even more preferably not less than 0.03 part by mass on the basis of 100 parts by mass of a total amount of the phthalic acid raw material and the alcohol raw material which are charged into a reactor from the viewpoint of allowing the catalyst to sufficiently exhibit a catalytic activity thereof, and is also preferably not more than 2 parts by mass, more preferably not more than 1 part by mass and even more preferably not more than 0.5 part by mass on the basis of 100 parts by mass of a total amount of the phthalic acid raw material and the alcohol raw material from the viewpoint of improving efficiency of addition of the catalyst.

(Reaction Temperature, Reaction Pressure, Etc.)

The esterification reaction may be conducted under reflux of the alcohol raw material using a known reaction apparatus equipped with a facility capable of refluxing the alcohol raw material therethrough.

The reaction temperature may vary depending upon the kind of the alcohol raw material used, etc., and is preferably not lower than 60° C., more preferably not lower than 100° C. and even more preferably not lower than 150° C. from the viewpoint of high reactivity, and is also preferably not higher than 280° C., more preferably not higher than 250° C. and even more preferably not higher than 230° C. from the viewpoint of high yield of the esterification reaction product. When the reaction temperature is not lower than 60° C., the esterification reaction is allowed to proceed at a high reaction rate. When the reaction temperature is not higher than 280° C., it is possible to suppress production of undesirable reaction by-products.

The reaction pressure is usually not less than 13.3 kPa, and preferably not more than normal pressures. The reaction pressure can be controlled according to a vapor pressure of the alcohol raw material used in the esterification reaction.

More specifically, the reaction pressure may be controlled to a pressure at which the reaction mixture is maintained in a boiled state, and besides, it is preferred that the reaction pressure is controlled to a pressure at which water by-produced can be removed out of the system.

The reaction time may vary depending upon the kinds of the phthalic acid raw material and the alcohol raw material used, the reaction temperature, the amount of the catalyst used in the esterification reaction, etc., and is preferably not less than 1 hour and more preferably not less than 2 hours from the viewpoint of high reactivity. If the reaction time is sufficiently long, it is possible to reduce a load applied in the step of separating the unreacted phthalic acid raw material or a phthalic acid monoester as a reaction intermediate product. On the other hand, from the viewpoint of high yield of the esterification reaction product, the reaction time is preferably not more than 24 hours and more preferably not more than 10 hours. If the reaction time is short, it is possible to suppress production of undesirable by-products and improve quality of the didecyl phthalates produced.

(Additional Treatments)

In the esterification reaction, under the aforementioned reaction conditions, water produced in the reaction is removed out of the reaction system by azeotropic distillation with the alcohol raw material to enhance the reaction rate near to 100%, and an excessive amount of the alcohol raw material is separated from the reaction product. The resulting reaction mixture is then subjected to additional treatments by known methods such as alkali cleaning, water washing, adsorption of impurities, distillation, etc., to obtain purified didecyl phthalates.

The thus obtained didecyl phthalates (esterification reaction condensate) may be used as the plasticizer that is to be incorporated in the halogen-based resin.

<Halogen-Based Resin>

The halogen-based resin used in the present invention means a homopolymer or a copolymer of a halogen-containing monomer, or a polymer that is modified with a halogen. Specific examples of the halogen-based resin include at least one resin selected from the group consisting of a vinyl chloride-based resin, polyvinylidene chloride, chlorinated polyethylene, chlorinated polypropylene, chloro-sulfonated polyethylene, a chloroprene rubber, and the like.

(Vinyl Chloride-Based Resin)

Examples of the vinyl chloride-based resin include a vinyl chloride homopolymer as well as a copolymer of vinyl chloride with a monomer copolymerizable with the vinyl chloride (hereinafter also referred to as a "vinyl chloride copolymer"), a graft copolymer obtained by graft-copolymerizing vinyl chloride to a polymer other than the vinyl chloride copolymer, and the like.

The aforementioned monomer copolymerizable with vinyl chloride may include those monomers having a reactive double bond in a molecule thereof. Examples of the monomer copolymerizable with vinyl chloride include α-olefins such as ethylene, propylene, butylene, etc.; vinyl esters such as vinyl acetate, vinyl propionate, etc.; vinyl ethers such as butyl vinyl ether, cetyl vinyl ether, etc.; unsaturated carboxylic acids such as acrylic acid, methacrylic acid, etc.; esters of acrylic acid or methacrylic acid such as methyl acrylate, ethyl methacrylate, phenyl methacrylate, etc.; aromatic vinyl compounds such as styrene, α-methyl styrene, etc.; halogenated vinyl compounds such as vinylidene chloride, vinyl fluoride, etc.; N-substituted maleimides such as N-phenyl maleimide, N-cyclohexyl maleimide, etc.; and the like.

In addition, as the polymer other than the vinyl chloride copolymer, there may used those polymers to which vinyl chloride can be graft-copolymerized. Examples of the polymer other than the vinyl chloride copolymer include an ethylene-vinyl acetate copolymer, an ethylene-vinyl acetate-carbon monoxide copolymer, an ethylene-ethyl acrylate copolymer, an ethylene-ethyl acrylate-carbon monoxide copolymer, an ethylene-methyl methacrylate copolymer, an ethylene-propylene copolymer, an acrylonitrile-butadiene copolymer, a polyurethane and the like.

Of the aforementioned halogen-based resins, from the viewpoint of good flexibility, etc., preferred is at least one resin selected from the group consisting of vinyl chloride-based resins such as polyvinyl chloride, an ethylene-vinyl chloride copolymer, a vinyl acetate-vinyl chloride copolymer, a polyurethane-grafted polyvinyl chloride copolymer, etc., polyvinylidene chloride and a chloroprene rubber, and more preferred is at least one resin selected from the group consisting of polyvinyl chloride, polyvinylidene chloride and a chloroprene rubber.

Furthermore, the aforementioned halogen-based resin may be used in the form of a polymer blend in combination with a non-halogen-based resin such as polyethylene, an ethylene-propylene rubber, an ethylene-vinyl acetate copolymer, an ethylene-ethyl acrylate copolymer, an ethylene-methyl methacrylate copolymer, an ethylene-methyl acrylate copolymer, a nitrile rubber, a polyester, a thermoplastic polyurethane and the like.

[Plasticizer Composition for Halogen-Based Resin]

The plasticizer composition for a halogen-based resin according to the present invention contains the plasticizer for a halogen-based resin according to the present invention.

The content of the plasticizer in the plasticizer composition for a halogen-based resin is preferably not less than 40% by mass, more preferably not less than 50% by mass, even more preferably not less than 60% by mass, further even more preferably not less than 65% by mass and still further even more preferably not less than 70% by mass, and is also preferably not more than 100% by mass, more preferably not more than 95% by mass and even more preferably not more than 90% by mass, from the viewpoint of improving all of plasticizability, productivity, processability, kneading properties and heat resistance of the resulting resin composition.

The plasticizer composition for a halogen-based resin according to the present invention may be further used in combination with other known ester compounds unless the advantageous effects of the present invention are adversely affected by inclusion thereof. In addition, the plasticizer composition for a halogen-based resin may be further compounded with various additives such as a stabilizer, a processing aid, a colorant, a filler, an antioxidant, an ultraviolet absorber, an antistatic agent, a lubricant, etc., if required. The details of the additives will be described hereinlater.

[Halogen-Based Resin Composition]

The halogen-based resin composition of the present invention contains a halogen-based resin, and the plasticizer for a halogen-based resin according to the present invention or the plasticizer composition of the present invention.

The content of the plasticizer in the halogen-based resin composition may be appropriately determined according to the use and applications of the halogen-based resin composition. The content of the plasticizer in the halogen-based resin composition is preferably not less than 0.01 part by mass, more preferably not less than 0.1 part by mass, even more preferably not less than 1 part by mass, further even more preferably not less than 5 parts by mass and still further even more preferably not less than 10 parts by mass, and is also preferably not more than 200 parts by mass, more preferably not more than 150 parts by mass, even more preferably not more than 125 parts by mass, further even more preferably not more than 110 parts by mass and still further even more preferably not more than 100 parts by mass, on the basis of 100 parts by mass of the halogen-based resin, from the viewpoint of improving all of plasticizability, productivity, processability, kneading properties and heat resistance of the resulting resin composition.

The halogen-based resin composition of the present invention may be further used in combination with other known ester compounds unless the advantageous effects of the present invention are adversely affected by inclusion thereof. In addition, the halogen-based resin composition may be further compounded with various additives such as a stabilizer, a processing aid, a colorant, a filler, an antioxidant, an ultraviolet absorber, an antistatic agent, a lubricant, etc., if required.

Examples of the ester compounds that can be used in combination with the plasticizer of the present invention include esters obtained by using phthalic acid, terephthalic acid, isophthalic acid, benzoic acid, adipic acid, sebacic acid, azelaic acid, maleic acid, fumaric acid, succinic acid, itaconic acid, trimellitic acid, pyromellitic acid, phosphoric acid, cyclohexanecarboxylic acid, cyclohexanedicarboxylic acid, epoxidated cyclohexanecarboxylic acid, cyclohexenecarboxylic acid, cyclohexenedicarboxylic acid, furancarboxylic acid, furandicarboxylic acid, citric acid, epoxidated fatty acids, etc., as an acid component thereof, and esters obtained by using a polyhydric alcohol such as glycol, glycerin, pentaerythritol, etc., as an alcohol component thereof. Among these ester compounds, preferred are the esters of phthalic acid, adipic acid, trimellitic acid, phosphoric acid, etc.

Suitable examples of the phthalic acid esters include dibutyl phthalate, di-2-ethylhexyl phthalate, diisononyl phthalate, diundecyl phthalate, didodecyl phthalate, ditridecyl phthalate and the like. Suitable examples of the adipic acid esters include di-2-ethylhexyl adipate, diisononyl adipate, diisodecyl adipate, di-2-propylheptyl adipate, di-4-methyl-2-propylhexyl adipate and the like. Suitable examples of the trimellitic acid esters include tri-2-ethylhexyl trimellitate, triisodecyl trimellitate, tri-2-propylheptyl trimellitate, tri-4-methyl-2-propylhexyl trimellitate and the like. Suitable examples of the phosphoric acid esters include tri-2-ethylhexyl phosphate, tricresyl phosphate, tri-2-propylheptyl phosphate, tri-4-methyl-2-propylhexyl phosphate and the like.

The amount of the aforementioned ester compound used is preferably not more than 10% by mass on the basis of a total amount of the plasticizer.

Examples of the stabilizer include metal soap compounds such as lithium stearate, magnesium stearate, magnesium laurate, calcium ricinolate, calcium stearate, barium laurate, barium ricinolate, barium stearate, zinc octylate, zinc laurate, zinc ricinolate, zinc stearate, etc.; organotin-based compounds such as dimethyl tin bis-2-ethylhexyl thioglycolate, dibutyl tin maleate, dibutyl tin bis(butyl maleate), dibutyl tin laurate, etc.; antimony mercaptide compounds; and the like. The amount of the stabilizer compounded in the halogen-based resin composition is from 0.1 to 20 parts by mass on the basis of 100 parts by mass of the halogen-based resin.

Examples of the processing aid include liquid paraffin, a polyethylene wax, stearic acid, stearamide, ethylene bis (stearamide), butyl stearate, calcium stearate and the like. The amount of the processing aid compounded in the halogen-based resin composition is from 0.1 to 20 parts by mass on the basis of 100 parts by mass of the halogen-based resin.

Examples of the colorant include carbon black, lead sulfide, white carbon, titanium white, lithopone, red iron oxide, antimony sulfide, chrome yellow, chrome green, cobalt blue, molybdenum orange and the like. The amount of the colorant compounded in the halogen-based resin composition is from 1 to 100 parts by mass on the basis of 100 parts by mass of the halogen-based resin.

Examples of the filler include metal oxides such as calcium carbonate, silica, alumina, clay, talc, diatomaceous earth, ferrite, etc.; and fibers or powders of glass, carbon, metals, etc.; glass beads, graphite, aluminum hydroxide, barium sulfate, magnesium oxide, magnesium carbonate, magnesium silicate, calcium silicate, etc.; and the like. The amount of the filler compounded in the halogen-based resin composition is from 1 to 100 parts by mass on the basis of 100 parts by mass of the halogen-based resin.

Examples of the antioxidant include phenol-based compounds such as 2,6-di-tert-butyl phenol, tetrakis[methylene-3-(3,5-tert-butyl-4-hydroxy phenol)propionate]methane, 2-hydroxy-4-methoxy benzophenone, etc.; sulfur-based compounds such as alkyl disulfides, thiodipropionic acid esters, benzothiazole, etc.; phosphoric acid-based compounds such as trisnonylphenyl phosphite, diphenyl isodecyl phosphite, triphenyl phosphite, tris(2,4-di-tert-butylphenyl) phosphite, etc.; organometallic-based compounds such as zinc dialkyl dithiophosphates, zinc diaryl dithiophosphates, etc.; and the like. The amount of the antioxidant compounded in the halogen-based resin composition is from 0.2 to 20 parts by mass on the basis of 100 parts by mass of the halogen-based resin.

Examples of the ultraviolet absorber include salicylate-based compounds such as phenyl salicylate, p-tert-butyl phenyl salicylate, etc.; benzophenone-based compounds such as 2-hydroxy-4-n-octoxy benzophenone, 2-hydroxy-4-n-methoxy benzophenone, etc.; benzotriazole-based compounds such as 5-methyl-1H-benzotriazole, 1-dioctyl aminomethyl benzotriazole, etc.; cyanoacrylate-based compounds; and the like. The amount of the ultraviolet absorber compounded in the halogen-based resin composition is from 0.1 to 10 parts by mass on the basis of 100 parts by mass of the halogen-based resin.

Examples of the antistatic agent include anionic antistatic agents such as alkyl sulfonate-type antistatic agents, alkyl ether carboxylic acid-type antistatic agents and dialkyl sulfosuccinate-type antistatic agents; nonionic antistatic agents such as polyethylene glycol derivatives, sorbitan derivatives, diethanol amine derivatives, etc.; cationic antistatic agents such as quaternary ammonium salts, e.g., alkyl amide amine-type antistatic agents, alkyl dimethyl benzyl-type antistatic agents, etc., organic acid salts or hydrochloric acid salts, e.g., alkyl pyridinium-type antistatic agents, etc.; amphoteric antistatic agents such as alkyl betaine-type antistatic agents, alkyl imidazoline-type antistatic agents, etc.; and the like. The amount of the antistatic agent compounded in the halogen-based resin composition is from 0.1 to 10 parts by mass on the basis of 100 parts by mass of the halogen-based resin.

Examples of the lubricant include silicones, liquid paraffin, a paraffin wax, fatty acids such as stearic acid, lauric acid, etc., and metal salts thereof, fatty acid amides, fatty acid waxes, higher fatty acid waxes and the like. The amount of the lubricant compounded in the halogen-based resin composition is from 0.1 to 10 parts by mass on the basis of 100 parts by mass of the halogen-based resin.

The halogen-based resin composition of the present invention may be produced by compounding the halogen-based resin and the plasticizer of the present invention, if required together with various additives, while stirring using a stirring device such as a mortar mixer, a Henschel mixer, a Banbury mixer, a ribbon blender, etc., to thereby obtain a mixed powder of the halogen-based resin composition. In addition, the resulting mixed powder may be further melted and molded using a kneading machine such as a conical twin screw extruder, a parallel twin screw extruder, a single screw extruder, a co-kneader-type kneader, a roll kneader, etc., to thereby obtain a pellet-shaped or paste-like material of the halogen-based resin composition.

The mixed powder or pellets of the halogen-based resin composition produced by the aforementioned method can be formed into a desired shape by known methods such as extrusion molding, injection molding, calender molding, press molding, blow molding, etc. In addition, the paste-like material of the halogen-based resin composition can be formed into a desired shape by known methods such as spread molding, dipping molding, gravure molding, screen processing, etc.

The thus obtained resin composition of the present invention is useful as adhesives, sealants, paints, plastisol, foamed bodies, synthetic leather, pipes such as water pipes, etc., building materials, wall paper materials, floorings, floor covering materials, insulating materials, roof membrane materials, packaging materials such as food packaging films, etc., agricultural materials such as agricultural films, etc., substrate protecting materials, cloth covering materials, sheathing materials for electric cables, automobile interior materials, various leather products, various foamed products, general-purpose hoses, gaskets, packing, boots, toys, food packaging materials, medical products such as tubes, blood bags, etc., and the like.

The resin composition of the present invention exhibits excellent properties, i.e., is excellent in processability and heat resistance, and therefore is usefully used, in particular, as any material selected from the group consisting of a roof membrane material, an electric cable sheathing material and an automobile interior material.

Incidentally, the content of the plasticizer of the present invention in the halogen-based resin composition can be quantitatively determined by a gas chromatographic method as described in Examples below, etc. For example, 0.3 g of the resin composition is mixed and dissolved in 10 mL of tetrahydrofuran, and methanol is added to the resulting solution in an amount of about 50% by mass on the basis of the tetrahydrofuran to precipitate the halogen-based resin. Then, the resulting liquid phase is separated from the resin by filtration, and the solvent is removed therefrom, followed by drying and concentrating the obtained solution and subjecting the resulting dried and concentrated product to the aforementioned chromatographic method, etc.

With respect to the aforementioned embodiments, the present invention further provides the following aspects relating to the plasticizer for a halogen-based resin, the plasticizer composition for a halogen-based resin and the halogen-based resin composition.

<1> A plasticizer for a halogen-based resin which contains a mixture of didecyl phthalates each containing a linear or branched $C_{10}$ alkyl group, in which a content of di-n-decyl phthalate in the mixture is not less than 48 mol % and not more than 70 mol %.

<2> The plasticizer for a halogen-based resin according to the aspect <1>, wherein the mixture of the didecyl phthalates is in the from of an intermolecular condensation reaction product obtained by esterification reaction between a phthalic acid raw material and an alcohol raw material, and the phthalic acid raw material is preferably at least one compound selected from the group consisting of phthalic acid and phthalic anhydride, and more preferably phthalic anhydride.

<3> The plasticizer for a halogen-based resin according to the aspect <1> or <2>, wherein the $C_{10}$ alkyl group is derived from at least one alcohol selected from the group consisting of n-decanol, isodecanol, 2-propyl-1-heptanol and 4-methyl-2-propyl-1-hexanol.

<4> The plasticizer for a halogen-based resin according to any one of the aspects <1> to <3>, wherein the plasticizer contains the didecyl phthalate(s) other than di-n-decyl phthalate, and the didecyl phthalate(s) other than di-n-decyl phthalate is at least one compound selected from the group consisting of di-1-methylnonyl phthalate, di-1-ethyloctyl phthalate, di-1-propylheptyl phthalate, di-1-butylhexyl phthalate, di-isodecyl phthalate, di-2-propylheptyl phthalate, di-4-methyl-2-propylhexyl phthalate, n-decyl (1-methylnonyl) phthalate, n-decyl (1-ethyloctyl) phthalate, n-decyl (1-propylheptyl) phthalate, n-decyl (1-butylhexyl) phthalate, n-decyl (isodecyl) phthalate, n-decyl (2-propylheptyl) phthalate, n-decyl (4-methyl-2-propylhexyl) phthalate, isodecyl (2-propylheptyl) phthalate and isodecyl (4-methyl-2-propylhexyl) phthalate, and preferably at least one compound selected from the group consisting of di-2-propylheptyl phthalate and n-decyl (2-propylheptyl) phthalate.

<5> The plasticizer for a halogen-based resin according to any one of the aspects <1> to <4>, wherein the halogen-based resin is preferably at least one resin selected from the group consisting of a vinyl chloride resin, polyvinylidene chloride and a chloroprene rubber.

<6> The plasticizer for a halogen-based resin according to any one of the aspects <1> to <5>, wherein an amount of the alcohol raw material charged in the esterification reaction is preferably not less than 2.0 mol, more preferably not less than 2.1 mol, even more preferably not less than 2.2 mol and further even more preferably not less than 2.3 mol, and is also preferably not more than 10 mol, more preferably not more than 6 mol, even more preferably not more than 4 mol and further even more preferably not more than 3 mol, per 1 mol of the phthalic acid raw material.

<7> The plasticizer for a halogen-based resin according to any one of the aspects <1> to <6>, wherein a catalyst used in the esterification reaction is preferably an organic metal catalyst, more preferably at least one compound selected from the group consisting of an organic tin compound, an organic titanium compound and an organic zinc compound, even more preferably at least one compound selected from the group consisting of dimethyl tin oxide, monobutyl tin oxide, dibutyl tin oxide and dioctyl tin oxide, further even more preferably at least one compound selected from the group consisting of monobutyl tin oxide and dibutyl tin oxide, and still further even more preferably monobutyl tin oxide.

<8> The plasticizer for a halogen-based resin according to any one of the aspects <1> to <7>, wherein an amount of the catalyst used in the esterification reaction is preferably not less than 0.01 part by mass, more preferably not less than 0.02 part by mass and even more preferably not less than 0.03 part by mass, and is also preferably not more than 2 parts by mass, more preferably not more than 1 part by mass and even more preferably not more than 0.5 part by mass, on the basis of 100 parts by mass of a total amount of the phthalic acid raw material and the alcohol raw material which are charged into a reactor.

<9> The plasticizer for a halogen-based resin according to any one of the aspects <1> to <8>, wherein a reaction temperature used in the esterification reaction is preferably not lower than 60° C., more preferably not lower than 100° C. and even more preferably not lower than 150° C., and is also preferably not higher than 280° C., more preferably not higher than 250° C. and even more preferably not higher than 230° C.

<10> The plasticizer for a halogen-based resin according to any one of the aspects <1> to <9>, wherein the halogen-based resin is preferably at least one resin selected from the group consisting of a vinyl chloride-based resin, polyvinylidene chloride, chlorinated polyethylene, chlorinated polypropylene, chloro-sulfonated polyethylene and a chloroprene rubber, and more preferably at least one resin selected from the group consisting of a vinyl chloride-based resin, polyvinylidene chloride and a chloroprene rubber.

<11> A plasticizer composition for a halogen-based resin containing the plasticizer according to any one of the aspects <1> to <10>. <12> The plasticizer composition for a halogen-based resin according to the aspect <11>, wherein a content of the plasticizer in the composition is preferably not less than 40% by mass, more preferably not less than 50% by mass, even more preferably not less than 60% by mass, further even more preferably not less than 65% by mass and still further even more preferably not less than 70% by mass, and is also preferably not more than 100% by mass, more preferably not more than 95% by mass and even more preferably not more than 90% by mass.

<13> A halogen-based resin composition containing a halogen-based resin, and the plasticizer according to any one of the aspects <1> to <10> or the plasticizer composition according to the aspect <11> or <12>.

<14> The halogen-based resin composition according to the aspect <13>, wherein a content of the plasticizer in the composition is preferably not less than 0.01 part by mass, more preferably not less than 0.1 part by mass, even more preferably not less than 1 part by mass, further even more preferably not less than 5 parts by mass and still further even more preferably not less than 10 parts by mass, and is also preferably not more than 200 parts by mass, more preferably not more than 150 parts by mass, even more preferably not more than 125 parts by mass, further even more preferably not more than 110 parts by mass and still further even more preferably not more than 100 parts by mass, on the basis of 100 parts by mass of the halogen-based resin.

<15> The halogen-based resin composition according to the aspect <13> or <14>, for use in a roof membrane material, an electric cable sheathing material or an automobile interior material.

EXAMPLES

In the following Production Examples, Examples and Comparative Examples, the "part(s)" and "%" indicate "part(s) by mass" and "% by mass", respectively, unless otherwise specified.

Production Example 1 (Production of Plasticizer P1)

A 1 L-capacity four-necked flask was charged with 148.1 g (1.00 mol) of phthalic anhydride available from Kanto Chemical Co., Inc., 379.9 g (2.40 mol) of n-decanol "KALKOL 1098" (tradename) available from Kao Corporation and 0.15 g of monobutyl tin oxide available from Tokyo Chemical Industry Co., Ltd., and the contents of the flask were mixed and heated, and maintained at 230° C. for 2.5 hours to react the respective components with each other while distilling off water therefrom.

After completion of the reaction, the resulting reaction solution was cooled to 90° C., and then 0.2 g of 85% phosphoric acid, 1.5 g of amorphous synthetic magnesium silicate "KYOWARD 600S" (tradename) available from Kyowa Chemical Industry Co., Ltd., 1.0 g of activated carbon "CARBOLAFIN" (tradename) available from Japan EnviroChemicals, Ltd., and 1.0 g of activated clay "GALLEON EARTH" (tradename) available from Mizusawa Industrial Chemicals, Ltd., were added thereto, followed by stirring the resulting mixture at 90° C. for 1 hour. Thereafter, the resulting mixture was heated to 200° C. at which an excess amount of the n-decanol was distilled off therefrom under a reduced pressure of about 400 Pa. Then, the reaction pressure was returned to normal pressures, and the reaction mixture was cooled to 90° C. and subjected to suction filtration using a filter paper over which a filtering aid "RADIOLITE #700" (tradename) available from Showa Chemical Industry Co., Ltd., was laid, thereby obtaining a plasticizer P1 in the form of an esterification reaction condensate (a mixture of didecyl phthalates). The results are shown in Table 1.

Production Examples 2 to 8 (Production of Plasticizers P2 to P8)

The same procedure as in Production Example 1 was repeated except that the esterification reaction was conducted using the alcohol components and the acid components shown in Table 1, thereby obtaining plasticizers P2 to P8. The results are shown in Table 1.

The details of the respective components shown in Table 1 are as follows.

Phthalic acid: Phthalic anhydride available from Kanto Chemical Co., Inc.

Isophthalic acid: Available from Tokyo Chemical Industry Co., Ltd.

Terephthalic acid: available from FUJIFILM Wako Pure Chemical Corporation n-Decanol: "KALKOL 1098" (tradename) available from Kao Corporation As the 2-propyl heptanol and 4-methyl-2-propyl hexanol, there was used a mixture of 2-propyl heptanol/4-methyl-2-propyl hexanol (mass ratio: 95/5) "2-PROPYL HEPTANOL" (tradename) available from BASF.

<Measurement of Content of Di-n-Decyl Phthalate>

A 10% plasticizer solution prepared by dissolving the respective plasticizers obtained in the aforementioned Production Examples in n-hexane was subjected to the following gas chromatography in which a content of di-n-decyl phthalate in the respective plasticizers was quantitatively determined from an area ratio of a peak of a chromatogram obtained thereby.

Measuring apparatus: "Agilent 6890N" (gas chromatograph) available from Agilent Technologies Japan, Ltd.
Column: "DB-1ht" (length: 30 m; inner diameter: 0.25 mm; film thickness: 0.10 μm) available from Agilent Technologies Japan, Ltd.
Carrier gas: He (constant flow mode)
Split ratio: 50:1          Detector: FID
Injection port temperature: 330° C.   Detector temperature: 330° C.
Measuring temperature conditions: 100° C. → temperature rise at 10° C./min → maintained at 350° C. for 10 minutes
Detection sensitivity: Retrieval rate, 20 Hz
Minimum peak width, 0.01 min
Amount injected: 1 μL (split method)
Quantitative determination of di-n-decyl phthalate:

Using a purified di-n-decyl phthalate, a detection time thereof was measured to previously determine a detection time of the di-n-decyl phthalate to be measured. In the measurement, a ratio of a peak area of the detection time of the di-n-decyl phthalate to a whole area thereof except for peaks detected for a short period of time which were derived from n-hexane and unreacted compounds, was determined and calculated.

(2) Using the aforementioned plasticizers P1 to P9 as well as the following plasticizer compositions 10 to 13 respectively prepared from the combination of plasticizers selected from the plasticizers P1, P2, P4, P6 and P9, non-molded sheets and molded sheets formed of a vinyl chloride resin were produced by the following methods, and evaluated with respect to plasticizability, productivity, processability, kneading properties and heat resistance thereof by the following evaluation methods. The results are shown in Table 2.

Plasticizer composition 10: Mixture of plasticizer P1 (55 parts) and plasticizer P2 (45 parts)
Plasticizer composition 11: Mixture of plasticizer P4 (60 parts) and plasticizer P9 (40 parts)
Plasticizer composition 12: Mixture of plasticizer P4 (40 parts) and plasticizer P9 (60 parts)
Plasticizer composition 13: Mixture of plasticizer P1 (20 parts) and plasticizer P6 (80 parts)

<Production of Vinyl Chloride Resin Non-Molded Sheet>

One hundred parts of a vinyl chloride resin "ZEST1400" (tradename; average polymerization degree: 1400) available

TABLE 1

| | | | Production Examples | | | | | | | |
|---|---|---|---|---|---|---|---|---|---|---|
| | | | 1 | 2 | 3 | 4 | 5 | 6 | 7 | 8 |
| Kind of plasticizer | | | P1 | P2 | P3 | P4 | P5 | P6 | P7 | P8 |
| Content of di-n-decyl phthalate (mol %) | | | 100 | 0 | 60 | 55 | 50 | 45 | 0 | 0 |
| Amount charged (g) | Acid component | Phthalic anhydride | 148.1 (1.00) | 148.1 (1.00) | 148.1 (1.00) | 148.1 (1.00) | 148.1 (1.00) | 148.1 (1.00) | — | — |
| | | Isophthalic acid | — | — | — | — | — | — | 166.1 (1.00) | — |
| | | Terephthalic acid | — | — | — | — | — | — | — | 166.1 (1.00) |
| | Alcohol content ($C_{10}$) | n-Decanol | 379.9 (2.40) | — | 294.4 (1.86) | 284.9 (1.80) | 269.0 (1.70) | 254.5 (1.61) | 294.4 (1.86) | 294.4 (1.86) |
| | | 2-Propyl heptanol** | — | 360.9 (2.28) | 81.2 (0.51) | 90.4 (0.57) | 105.4 (0.67) | 119.1 (0.75) | 81.2 (0.51) | 81.2 (0.51) |
| | | 4-Methyl-2-propyl heptanol** | — | 19.0 (0.12) | 4.3 (0.03) | 4.8 (0.03) | 5.6 (0.04) | 6.3 (0.04) | 4.3 (0.03) | 4.3 (0.03) |

Note
*Values in respective parentheses represent molar amounts.
**Mixture of 2-propyl heptanol/4-methyl-2-propyl hexanol (mass ratio: 95/5)

Examples 1 to 7 and Comparative Examples 1 to 5

(1) The plasticizers P1 to P8 obtained in Production Examples 1 to 8, respectively, and the plasticizer P9 were prepared. The details of the plasticizers P1 to P9 are as follows.

| Plasticizer P1: | Di-n-decyl phthalate | 100 mol % |
|---|---|---|
| Plasticizer P2: | Di-2-propylheptyl phthalate | 95 mol % |
| | 2-Propylheptyl (4-methyl-2-propylhexyl) phthalate | 4.8 mol % |
| Plasticizer P3: | Di-n-decyl phthalate | 60 mol % |
| | n-Decyl (2-propylheptyl) phthalate | 33 mol % |
| Plasticizer P4: | Di-n-decyl phthalate | 55 mol % |
| | n-Decyl (2-propylheptyl) phthalate | 36 mol % |
| Plasticizer P5: | Di-n-decyl phthalate | 50 mol % |
| | n-Decyl (2-propylheptyl) phthalate | 39 mol % |
| Plasticizer P6: | Di-n-decyl phthalate | 45 mol % |
| | n-Decyl (2-propylheptyl) phthalate | 42 mol % |
| Plasticizer P7: | Di-n-decyl isophthalate | 60 mol % |
| | n-Decyl (2-propylheptyl) isophthalate | 33 mol % |
| Plasticizer P8: | Di-n-decyl terephthalate | 60 mol % |
| | n-Decyl (2-propylheptyl) terephthalate | 33 mol % |
| Plasticizer P9: | Tri-2-ethylhexyl trimellitate | 100 mol % |

("TRIMEX T-08NB" (tradename) available from Kao Corporation)

from ShinDai-Ichi Vinyl Corporation were mixed with 60 parts of the respective plasticizers or plasticizer compositions shown in Table 2, 2 parts of a Ca/Mg/Zn-based stabilizer for vinyl chloride resins "ADEKASTAB RUP-103" (tradename) available from ADEKA Corporation and 0.5 part of a lubricant "LUNAC S-70V" (tradename) available from Kao Corporation while stirring with a stirring rod at room temperature. Thereafter, the resulting resin composition was kneaded and gelled at 170° C. and a rotating speed of 17 rpm using a 4-inch open roll-type kneader available from Nishimura Machinery Co., Ltd., and then the gelled resin composition was further continuously kneaded for 10 minutes, thereby obtaining a non-molded sheet.

<Production of Vinyl Chloride Resin Molded Sheet>

The respective non-molded sheets produced above were preheated at 170° C. for 5 minutes and then pressed under a pressure of 20 MPa for 2 minutes, thereby obtaining a 0.8 mm-thick resin molded sheet.

<Evaluation Methods>

(1) Evaluation of Plasticizability

The vinyl chloride resin molded sheet was punched into a #3 dumbbell shape according to the JIS standard (JIS K 6251) to prepare a test specimen. The thus prepared test specimen was subjected to tensile test using a tensile tester "AUTOGRAPH AGS-X" (tradename) available from Shimadzu Corporation to measure an elongation at break of the test specimen (breaking elongation (%)). The larger the breaking elongation value becomes, the higher the elongation of the test specimen is and therefore the more excellent the plasticizability thereof is.

(2) Evaluation of Productivity

In the production of the vinyl chloride resin non-molded sheet, the time elapsed until the resin composition was gelled (gelling time) was measured. The shorter gelling time indicates a more excellent productivity of the resin sheet.

The "gelling time" as used herein is defined as the time required until visually observing such a condition that when a powder obtained by mixing the vinyl chloride resin and the plasticizer at an ordinary temperature is heated and kneaded using a kneader, the mixed powder is melted and homogenized into a liquid state as a whole.

(3) Evaluation of Processability

In order to evaluate a load applied to a motor during the gelling time, a current value (A) of the motor was measured. The smaller current value (A) of the motor indicates a lower load applied to the kneader upon processing the resin composition and a smaller heat history up to completion of the kneading, and therefore a more excellent processability of the resin composition.

(4) Evaluation of Kneading Properties

In the production of the vinyl chloride resin molded sheet, whether any residual resin adhered to a mold was present or not was ascertained by visual observation to evaluate kneading properties of the resin composition according to the following evaluation ratings.

(Evaluation Ratings)

1: Adhesion of the resin onto a mold was apparently recognized by visual observation.

0: No adhesion of the resin onto a mold was recognized by visual observation.

If the resin composition was uniformly kneaded, no residual resin adhered to the mold was present. However, if the resin composition was non-uniformly kneaded, when releasing the molded resin from the mold, some resin was caused to remain in the mold without being entirely released therefrom, so that contaminants were produced by the residual resin upon molding the subsequent resin sheets.

(5) Evaluation of Heat Resistance

A test specimen formed of a halogen-based resin molded sheet punched into a #3 dumbbell shape as prescribed in the JIS standard (JIS K 6251) was allowed to stand at 100° C. for 100 hours in a Geer oven-type aging tester "AG-103" (tradename) available from Ueshima Seisakusho Co., Ltd., as prescribed in JIS K 7212 to measure a rate (%) of reduction of a mass thereof between before and after the aging test. The closer to zero the reduction rate becomes, the more excellent the heat resistance of the test specimen is.

TABLE 2

| | Plasticizer or plasticizer composition | Plasticizer Content of di-n-decyl phthalate (mol %) | Plasticizer composition Content of plasticizer (% by mass) | Plasticizer composition Content of di-n-decyl phthalate (mol %) |
|---|---|---|---|---|
| Example 1 | Plasticizer P3 | 60 | 100 | 60 |
| Example 2 | Plasticizer P4 | 55 | 100 | 55 |
| Example 3 | Plasticizer P5 | 50 | 100 | 50 |
| Example 4 | Plasticizer composition 10 P1/P2 (55/45)* | 55 | 100 | 55 |
| Example 5 | Plasticizer composition 11 P4/P9 (60/40)* | 55 | 60 | 36 |
| Example 6 | Plasticizer composition 12 P4/P9 (40/60)* | 55 | 40 | 25 |
| Example 7 | Plasticizer composition 13 P1/P6 (20/80)* | 56 | 100 | 56 |
| Comparative Example 1 | Plasticizer P1 | 100 | 0 | 100 |
| Comparative Example 2 | Plasticizer P2 | 0 | 0 | 0 |
| Comparative Example 3 | Plasticizer P6 | 45 | 0 | 45 |
| Comparative Example 4 | Plasticizer P7 | 0 | 0 | 0 |
| Comparative Example 5 | Plasticizer P8 | 0 | 0 | 0 |

| | Evaluation results | | | | |
|---|---|---|---|---|---|
| | Plasticizability Breaking elongation (%) | Productivity Gelling time (sec) | Processability Current value (A) | Kneading properties Residual resin (visual observation) | Heat resistance Rate of reduction of mass (%) |
| Example 1 | 370 | 90 | 9.8 | 0 | −0.83 |
| Example 2 | 369 | 87 | 10.0 | 0 | −0.84 |
| Example 3 | 386 | 85 | 10.1 | 0 | −0.87 |
| Example 4 | 377 | 82 | 10.2 | 0 | −1.20 |
| Example 5 | 386 | 93 | 9.6 | 0 | −0.77 |
| Example 6 | 387 | 105 | 8.9 | 0 | −0.72 |

TABLE 2-continued

| | | | | | |
|---|---|---|---|---|---|
| Example 7 | 369 | 87 | 10.0 | 0 | −0.84 |
| Comparative Example 1 | 357 | 90 | 10.3 | 0 | −0.57 |
| Comparative Example 2 | 370 | 55 | 13.1 | 0 | −2.26 |
| Comparative Example 3 | 385 | 70 | 12.0 | 0 | −0.98 |
| Comparative Example 4 | 347 | 195 | 7.6 | 1 | −0.16 |
| Comparative Example 5 | 319 | 120 | 8.5 | 1 | −3.23 |

Note
*Values in respective parentheses represent mass ratios of plasticizers.

From Table 2, it was confirmed that the plasticizers and plasticizer compositions obtained in Examples 1 to 7 had sufficient plasticization performance (breaking elongation) when compounded in the halogen-based resin, and exhibited excellent effects of improving productivity, processability, kneading properties and heat resistance as compared to the plasticizers obtained in Comparative Examples 1 to 5.

In addition, the halogen-based resin composition containing the plasticizer of the present invention was excellent in processability and heat resistance, and therefore useful, in particular, as a roof membrane material, an electric cable sheathing material, an automobile interior material and the like.

INDUSTRIAL APPLICABILITY

In accordance with the present invention, it is possible to provide a plasticizer for a halogen-based resin which has an excellent plasticization effect on a halogen-based resin, and at the same time, can exhibit excellent effects of improving all of productivity processability, kneading properties and heat resistance without deterioration in the respective properties, and a halogen-based resin composition containing the plasticizer.

The invention claimed is:
1. A plasticizer for a halogen-based resin comprising a mixture of didecyl phthalates each comprising a linear or branched $C_{10}$ alkyl group, in which a content of di-n-decyl phthalate is not less than 48 mol % and not more than 70 mol %, and the remainder of the mixture of didecyl phthalates contains one or more additional didecyl phthalate(s) other than di-n-decyl phthalate.
2. The plasticizer for a halogen-based resin according to claim 1, wherein the $C_{10}$ alkyl group is derived from a combination of n-decanol and at least one alcohol selected from the group consisting of isodecanol, 2-propyl-1-heptanol and 4-methyl-2-propyl-1-hexanol.
3. The plasticizer for a halogen-based resin according to claim 1, wherein the one or more additional didecyl phthalate(s) other than di-n-decyl phthalate is at least one compound selected from the group consisting of di-1-methylnonyl phthalate, di-1-ethyloctyl phthalate, di-1-propylheptyl phthalate, di-1-butylhexyl phthalate, di-isodecyl phthalate, di-2-propylheptyl phthalate, di-4-methyl-2-propylhexyl phthalate, n-decyl (1-methylnonyl) phthalate, n-decyl (1-ethyloctyl) phthalate, n-decyl (1-propylheptyl) phthalate, n-decyl (1-butylhexyl) phthalate, n-decyl (isodecyl) phthalate, n-decyl (2-propylheptyl) phthalate, n-decyl (4-methyl-2-propylhexyl) phthalate, isodecyl (2-propylheptyl) phthalate, isodecyl (4-methyl-2-propylhexyl) phthalate, and 2-propylheptyl (4-methyl-2-propylhexyl) phthalate.

4. The plasticizer for a halogen-based resin according to claim 1, wherein the one or more additional didecyl phthalate(s) other than di-n-decyl phthalate is at least one compound selected from the group consisting of di-2-propylheptyl phthalate, n-decyl (2-propylheptyl) phthalate, and 2-propylheptyl (4-methyl-2-propylhexyl) phthalate.
5. The plasticizer for a halogen-based resin according to claim 1, wherein the mixture of didecyl phthalates is represented by the following general formula (1):

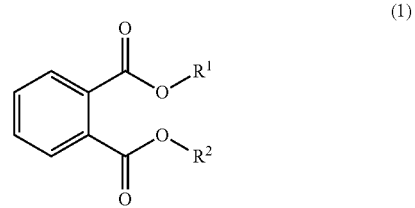

wherein, $R^1$ and $R^2$ are each independently a linear or branched $C_{10}$ alkyl group, and
the mixture of didecyl phthalates that are each represented by the general formula (1) is in the form of a mixture containing the following compounds (i) to (iii),
(i) di-n-decyl phthalate in which the substituent groups $R^1$ and $R^2$ both are an n-decyl group,
(ii) a compound of the formula (1) in which one of the substituent groups $R^1$ and $R^2$ is an n-decyl group and the other thereof is a branched decyl group, and
(iii) a compound of the formula (1) in which both of the substituent groups $R^1$ and $R^2$ are branched decyl groups.
6. The plasticizer for a halogen-based resin according to claim 5, wherein the branched decyl group includes at least one alcohol selected from the group consisting of 1-methylnonyl group, 1-ethyloctyl group, 1-propylheptyl group, 1-butylhexyl group, isodecyl group, 2-propylheptyl group, and 4-methyl-2-propylhexyl group.
7. A plasticizer composition for a halogen-based resin comprising the plasticizer according to claim 1, wherein the plasticizer in the composition is not less than 40% by mass and not more than 100% by mass.
8. A halogen-based resin composition comprising a halogen-based resin, and the plasticizer according to claim 1.
9. The halogen-based resin composition according to claim 8, wherein a content of the plasticizer in the composition is not less than 0.01 part by mass and not more than 200 parts by mass on the basis of 100 parts by mass of the halogen-based resin.
10. The halogen-based resin composition according to claim 8, wherein the halogen-based resin is at least one resin selected from the group consisting of a vinyl chloride-based resin, polyvinylidene chloride, chlorinated polyethylene, chlorinated polypropylene, chloro-sulfonated polyethylene, and a chloroprene rubber.

11. A method for producing a plasticizer for a halogen-based resin comprising a mixture of didecyl phthalates each comprising a linear or branched $C_{10}$ alkyl group, wherein the mixture of the didecyl phthalates is obtained by an esterification reaction between a phthalic acid raw material and an alcohol raw material, the phthalic acid raw material is at least one compound selected from the group consisting of phthalic acid and phthalic anhydride, and comprising the following methods (i) or (ii):

(i) a method of producing the plasticizer by using in the esterification reaction a mixed decanol as a raw material in which a content of n-decanol in the alcohol raw material is precisely controlled such that a content of di-n-decyl phthalate in the plasticizer is not less than 48 mol % and not more than 70 mol % after producing the plasticizer, and (ii) a method of producing the plasticizer by mixing di-n-decyl phthalate and one or more additional didecyl phthalate(s) other than di-n-decyl phthalate such that a content of the di-n-decyl phthalate in the plasticizer is adjusted to a predetermined value of not less than 48 mol % and not more than 70 mol %.

12. The method for producing a plasticizer for a halogen-based resin according to claim 11, wherein, in the method (i), mixed decanol is consisting of n-decanol and a branched alcohol including at least one alcohol selected from the group consisting of isodecanol, 2-decanol, 3-decanol, 4-decanol, 5-decanol, 2-propyl-1-heptanol, and 4-methyl-2-propyl-1-hexanol.

13. The method for producing a plasticizer for a halogen-based resin according to claim 11, wherein, in the method (i), the alcohol raw material consists of n-decanol and a branched alcohol including at least one alcohol selected from the group consisting of 2-propyl-1-heptanol and 4-methyl-2-propyl-1-hexanol .

14. The method for producing a plasticizer for a halogen-based resin according to claim 11, wherein, in the method (ii), the one or more additional didecyl phthalate(s) other than di-n-decyl phthalate is at least one compound selected from the group consisting of di-1-methylnonyl phthalate, di-1-ethyloctyl phthalate, di-1-propylheptyl phthalate, di-1-butylhexyl phthalate, di-isodecyl phthalate, di-2-propylheptyl phthalate, di-4-methyl-2-propylhexyl phthalate, n-decyl (1-methylnonyl) phthalate, n-decyl (1-ethyloctyl) phthalate, n-decyl (1-propylheptyl) phthalate, n-decyl (1-butylhexyl) phthalate, n-decyl (isodecyl) phthalate, n-decyl (2-propylheptyl) phthalate, n-decyl (4-methyl-2-propylhexyl) phthalate, isodecyl (2-propylheptyl) phthalate, isodecyl (4-methyl-2-propylhexyl) phthalate, and 2-propylheptyl (4-methyl-2-propylhexyl) phthalate.

15. The method for producing a plasticizer for a halogen-based resin according to claim 11, wherein, in the method (ii), the one or more additional didecyl phthalate(s) other than di-n-decyl phthalate is at least one compound selected from the group consisting of di-2-propylheptyl phthalate, n-decyl (2-propylheptyl) phthalate, and 2-propylheptyl (4-methyl-2-propylhexyl) phthalate.

* * * * *